United States Patent
Morgan

[11] Patent Number: 5,879,038
[45] Date of Patent: Mar. 9, 1999

[54] CONTACT LENS HANDLING DEVICE

[76] Inventor: Richard Roderick Morgan, Apt. 306, 734 Lampson Street, Victoria, Prov. Of B.C. V9A-6A6, Canada

[21] Appl. No.: 993,110

[22] Filed: Dec. 18, 1997

[51] Int. Cl.$^6$ ....................................................... A61F 9/00
[52] U.S. Cl. ............................ 294/1.2; 294/25; 294/64.1
[58] Field of Search ........................... 294/1.2, 25, 64.1; 206/5.1; 606/107

[56] References Cited

U.S. PATENT DOCUMENTS

| | | | |
|---|---|---|---|
| 450,447 | 4/1891 | Buchwalter | 294/25 |
| 1,316,436 | 9/1919 | Feeney | 294/25 |
| 2,935,354 | 5/1960 | Chapman | 294/25 |
| 3,132,887 | 5/1964 | Martinez | 294/1.2 |
| 3,490,806 | 1/1970 | Lopez-Calleja et al. | 294/1.2 |
| 4,126,345 | 11/1978 | List | 294/1.2 |
| 4,167,283 | 9/1979 | Feldman | 294/1.2 |
| 4,387,921 | 6/1983 | Licata | 294/25 |
| 4,466,313 | 8/1984 | Gardner | 294/25 |
| 5,348,358 | 9/1994 | Selick | 294/1.2 |

FOREIGN PATENT DOCUMENTS

| | | | |
|---|---|---|---|
| 3822-654 | 1/1990 | Germany | 294/1.2 |

*Primary Examiner*—Dean Kramer

[57] ABSTRACT

A device for handling a contact lens during insertion and removal thereof. The inventive device includes a finger mounting assembly for positioning over a finger of a human hand. A lens engaging assembly is mounted to a tip of the finger mounting assembly for engaging a contact lens. The lens engaging assembly can include a concave receiver for engaging an exterior surface of a lens and a pneumatic bulb positioned in fluid communication with the receiver for securing the lens thereto by vacuum.

1 Claim, 3 Drawing Sheets

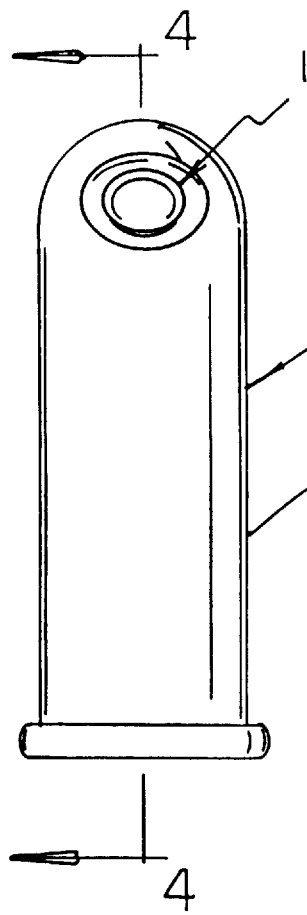
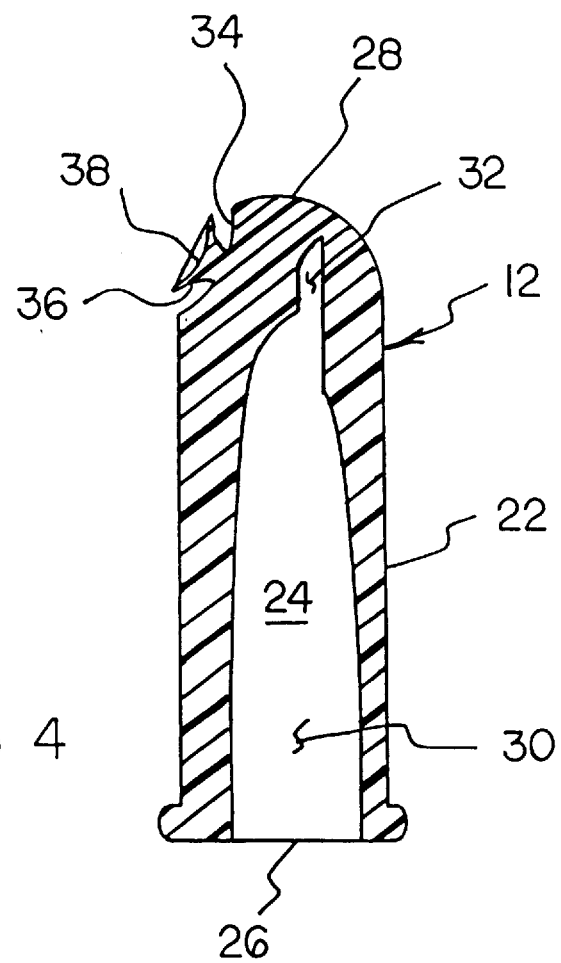

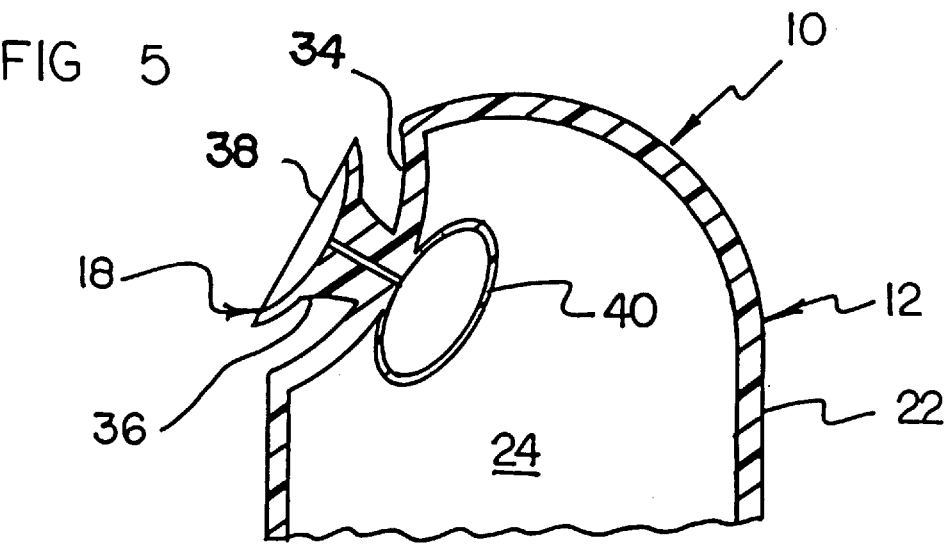
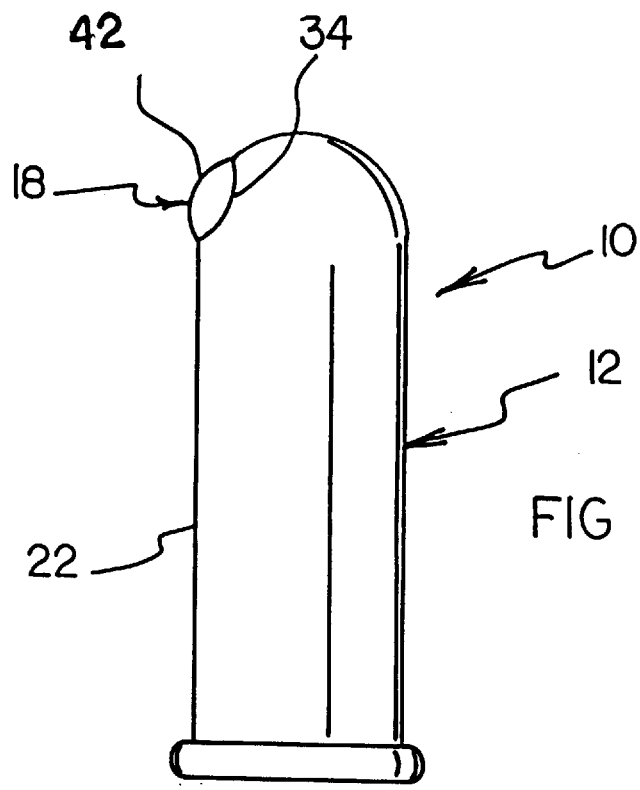

CONTACT LENS HANDLING DEVICE

BACKGROUND OF THE INVENTION

1. Field of the Invention

The present invention relates to ophthalmic lens holders and more particularly pertains to a contact lens handling device for handling a contact lens during insertion and removal thereof.

2. Description of the Prior Art

The use of ophthalmic lens holders is known in the prior art. More specifically, ophthalmic lens holders heretofore devised and utilized are known to consist basically of familiar, expected and obvious structural configurations, notwithstanding the myriad of designs encompassed by the crowded prior art which have been developed for the fulfillment of countless objectives and requirements.

Known prior art ophthalmic lens holders include U.S. Pat. No. 5,246,259; U.S. Pat. No. 4,565,396; U.S. Pat. No. 4,512,601; U.S. Pat. No. 4,387,921; U.S. Pat. No. 4,200,320; and U.S. Pat. No. 4,167,283.

While these devices fulfill their respective, particular objectives and requirements, the aforementioned patents do not disclose a contact lens handling device for handling a contact lens during insertion and removal thereof which includes a finger mounting means for positioning over a finger of a human hand, and a lens engaging means mounted to a tip of the finger mounting means for engaging a contact lens, wherein the lens engaging means can include a concave receiver for engaging an exterior surface of a lens and a pneumatic bulb positioned in fluid communication with the receiver for securing the lens thereto by vacuum.

In these respects, the contact lens handling device according to the present invention substantially departs from the conventional concepts and designs of the prior art, and in so doing provides an apparatus primarily developed for the purpose of handling a contact lens during insertion and removal thereof.

SUMMARY OF THE INVENTION

In view of the foregoing disadvantages inherent in the known types of ophthalmic lens holders now present in the prior art, the present invention provides a new contact lens handling device construction wherein the same can be utilized for handling a contact lens. As such, the general purpose of the present invention, which will be described subsequently in greater detail, is to provide a new contact lens handling device apparatus and method which has many of the advantages of the ophthalmic lens holders mentioned heretofore and many novel features that result in a contact lens handling device which is not anticipated, rendered obvious, suggested, or even implied by any of the prior art ophthalmic lens holders, either alone or in any combination thereof.

To attain this, the present invention generally comprises a device for handling a contact lens during insertion and removal thereof. The inventive device includes a finger mounting assembly for positioning over a finger of a human hand. A lens engaging assembly is mounted to a tip of the finger mounting assembly for engaging a contact lens. The lens engaging assembly can include a concave receiver for engaging an exterior surface of a lens and a pneumatic bulb positioned in fluid communication with the receiver for securing the lens thereto by vacuum.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new contact lens handling device apparatus and method which has many of the advantages of the ophthalmic lens holders mentioned heretofore and many novel features that result in a contact lens handling device which is not anticipated, rendered obvious, suggested, or even implied by any of the prior art tool guides, either alone or in any combination thereof.

It is another object of the present invention to provide a new contact lens handling device which may be easily and efficiently manufactured and marketed.

It is a further object of the present invention to provide a new contact lens handling device which is of a durable and reliable construction.

An even further object of the present invention is to provide a new contact lens handling device which is susceptible of a low cost of manufacture with regard to both materials and labor, and which accordingly is then susceptible of low prices of sale to the consuming public, thereby making such contact lens handling devices economically available to the buying public.

Still yet another object of the present invention is to provide a new contact lens handling device which provides in the apparatuses and methods of the prior art some of the advantages thereof, while simultaneously overcoming some of the disadvantages normally associated therewith.

Still another object of the present invention is to provide a new contact lens handling device for handling a contact lens during insertion and removal thereof.

Yet another object of the present invention is to provide a new contact lens handling device which includes a finger mounting means for positioning over a finger of a human hand, and a lens engaging means mounted to a tip of the finger mounting means for engaging a contact lens, wherein the lens engaging means can include a concave receiver for engaging an exterior surface of a lens and a pneumatic bulb positioned in fluid communication with the receiver for securing the lens thereto by vacuum.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a front elevation view thereof.

FIG. 4 is a cross-sectional view taken along line 4—4 of FIG. 3.

FIG. 5 is a cross-sectional view of the invention including an alternative form of a lens engaging means.

FIG. 6 is a side elevation view of the invention including a further alternative form of the lens engaging means.

DESCRIPTION OF THE PREFERRED EMBODIMENT

Figure 1:
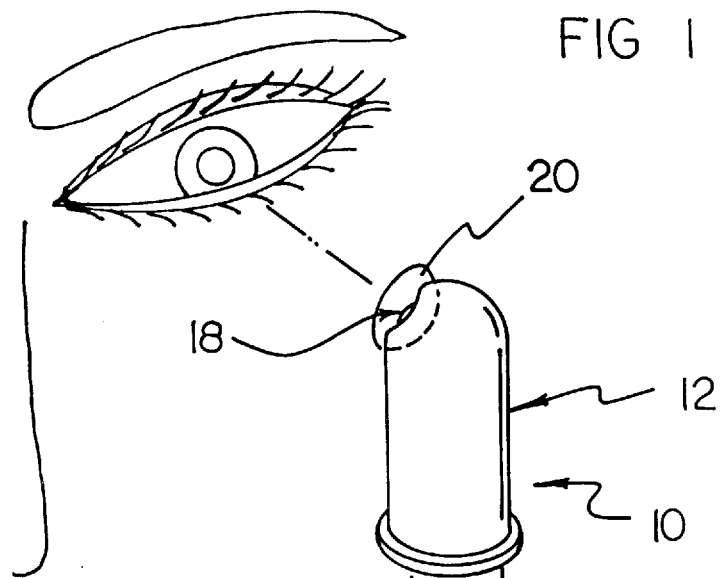
FIG. 1 is an isometric illustration of a contact lens handling device according to the present invention in use.

With reference now to the drawings, and in particular to FIGS. 1–6 thereof, a new contact lens handling device embodying the principles and concepts of the present invention and generally designated by the reference numeral 10 will be described.

More specifically, it will be noted that the contact lens handling device 10 comprises a finger mounting means 12 for securing to a finger 14 of a human hand 16 such as is shown in FIG. 1 of the drawings. A lens engaging means 18 is mounted to the finger mounting means 12 for engaging a contact lens 20 so as to permit ease of manual manipulation of the contact lens. By this structure, an individual can easily insert and/or remove the contact lens 20 relative to an eye absent a possibility of a fingernail of the finger accidentally engaging the eye.

Figure 2:
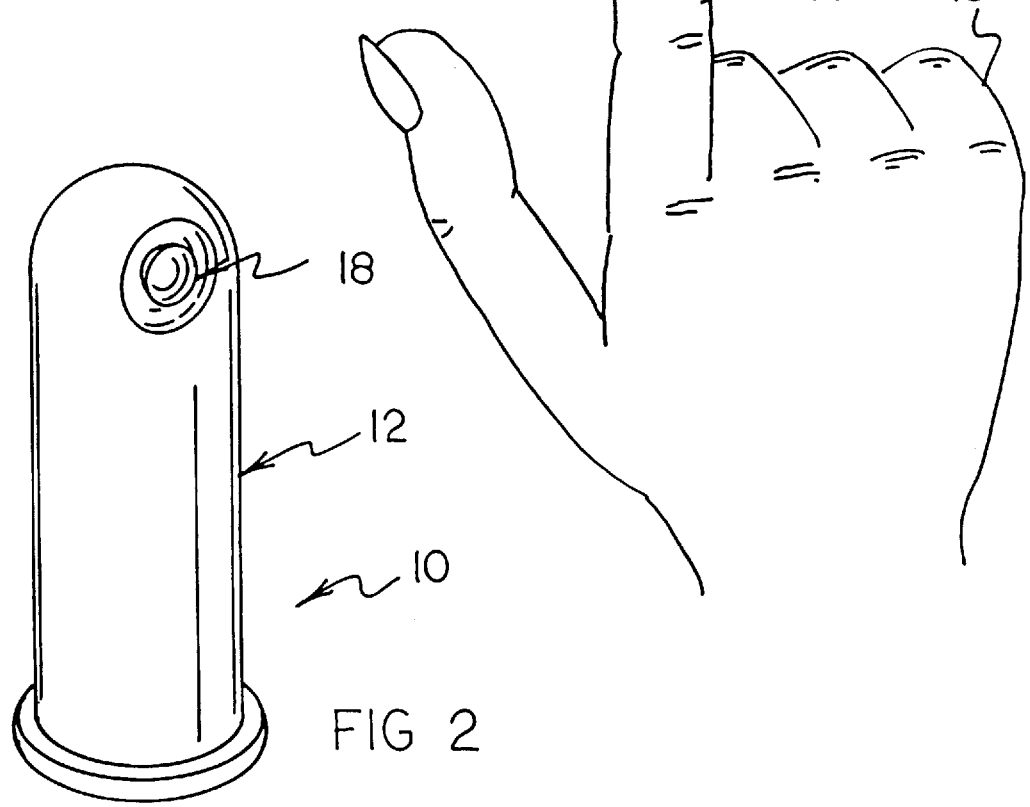
FIG. 2 is an isometric illustration of the invention, per se.

Referring now to FIGS. 2 through 4 wherein the present invention 10 is illustrated in detail, it can be shown that the finger mounting means 12 of the present invention 10 preferably comprises a cylindrical receiver 22 having a hollow interior space 24 positioned in communication with an open end 26 through which an individual's finger can be positioned thereinto. The cylindrical receiver 22 is further shaped so as to define a hemispherical closed end 28 oppositely oriented relative to the open end 26 thereof, with the lens engaging means 18 extending from the hemi-spherical closed end 28. As shown specifically in FIG. 4, the interior space 24 can be shaped so as to define a finger cavity 30 shaped to closely accommodate a human finger therewithin, and a fingernail cavity 32 projecting from within contiguous communication with the finger cavity 30 and longitudinally therefrom towards the hemi-spherical closed end 28. The fingernail cavity 32 is shaped so as to accommodate an elongated human fingernail therewithin such as is commonly worn by female individuals. By this structure, the finger mounting means 12 can securely accommodate and engage the human finger within the interior space 24. Further, an individual having an elongated fingernail projecting from the finger 14 can position such fingernail into the fingernail cavity 32 as needed.

With continuing reference to FIGS. 2 through 4, it can be shown that the lens engaging means 18 of the present invention 10 preferably comprises a concave panel 34 which is integrally or otherwise secured within a portion of the hemi-spherical closed end 28 of the cylindrical receiver 22 of the finger mounting means 12. A projection 36 extends from the concave panel 34 and continues to expand radially outward so as to define a concave receiver 38 within which an exterior surface of a contact lens 20 can be received as shown in FIG. 1 of the drawings. Preferably, the concave receiver 38 is oriented so as to extend at an oblique angle relative to a longitudinal axis directed centrally through the cylindrical receiver 22 so as to support the contact lens 20 at a desired angular orientation for insertion and/or removal relative to an eye as shown in FIG. 1 of the drawings.

Referring now to FIG. 5, it can be shown that an alternative form of the lens engaging means 18 further comprises a pneumatic bulb 40 mounted within the interior space 24 of the cylindrical receiver 22 of the finger mounting means 12. The pneumatic bulb 40 is positioned in fluid communication with an interior of the concave receiver 38 via an unlabelled conduit aperture extending through the projection 36. By this structure, the pneumatic bulb 40 can be manually operated by a finger 14 positioned within the device 10 so as to create a vacuum within the interior of the concave receiver 38 which causes the contact lens 20 to be retained within the concave receiver. As shown in FIG. 5, the pneumatic bulb 40 can be integrally or otherwise secured to the lens engaging means 18.

Referring now to FIG. 6, it can be shown that the lens engaging means 18 may alternatively be configured for supporting a contact lens upon an interior surface thereof to permit polishing or the like of an exterior surface of the contact lens. To this end, the lens engaging means 18 may simply comprise a convex receiver 42 projected from the concave panel 34 which is shaped so as to engage the interior surface of the contact lens 20. It should be noted that the alternative form of the lens engaging means 18 illustrated in FIG. 6 of the drawings may also include the pneumatic bulb 40 positioned in fluid communication with the convex receiver 42 via a conduit aperture directed therethrough so as to permit securement of the contact lens 20 to the convex receiver 42 by vacuum as described above.

In use, the contact lens handling device 10 of the present invention can be easily utilized for handling a contact lens during insertion and/or removal thereof. The present invention 10 thus operates to substantially eliminate a possibility of an individual's fingernail contacting the eye during manipulation of the contact lens 20 relative thereto. The various forms of the lens engaging means 18 permit the contact lens 20 to be secured to the device 10 by a variety of means and in a variety of orientations as desired by an end user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A contact lens handling device comprising:

a finger mounting means for securing to a finger of a human hand, the finger mounting means comprising a cylindrical receiver having a hollow interior space, and an open end positioned in communication with the hollow interior space, the cylindrical receiver being further shaped so as to define a hemi-spherical closed end oppositely oriented relative to the open end thereof;

a lens engaging means being mounted to and extending from the hemi-spherical closed end, the cylindrical receiver being shaped so as to define a finger cavity shaped to closely accommodate a human finger therewithin and a fingernail cavity projecting from contiguous communication with the finger cavity and longitudinally therefrom towards the hemi-spherical closed end of the cylindrical receiver, the fingernail cavity being shaped so as to accommodate an elongated human fingernail therewithin, and a concave panel secured within a portion of the hemi-spherical closed end of the cylindrical receiver of the finger mounting means;

the lens engaging means further comprising a projection extending from the hemi-spherical closed end of the cylindrical receiver, the projection continuing from the cylindrical receiver and expanding radially outward so as to define a concave receiver within which an exterior surface of a contact lens can be received, the concave receiver being oriented so as to extend at an oblique angle relative to a longitudinal axis directed centrally through the cylindrical receiver and with the projection extending from the concave panel of the cylindrical receiver, and the lens engaging means further comprising a pneumatic bulb mounted within the interior space of the cylindrical receiver of the finger mounting means, the pneumatic bulb being positioned in fluid communication with an interior of the concave receiver.

* * * * *